United States Patent [19]
Cheng et al.

[11] Patent Number: 5,891,892
[45] Date of Patent: Apr. 6, 1999

[54] SMALL MOLECULE BIARYL COMPOUNDS AS INHIBITORS OF ENDOTHELIN CONVERTING ENZYME

[75] Inventors: Xue-Min Cheng, Ann Arbor; Mark Alan Massa, Canton; William Chester Patt, Chelsea, all of Mich.

[73] Assignee: Warner-Lambert Company, Morris Plains, N.J.

[21] Appl. No.: 949,632

[22] Filed: Oct. 14, 1997

Related U.S. Application Data

[60] Provisional application No. 60/028,803 Oct. 29, 1996.
[51] Int. Cl.$^6$ .......................... A61K 31/44; C07D 417/04
[52] U.S. Cl. ......................... 514/340; 546/270.4
[58] Field of Search .......................... 546/270.4; 514/340

[56] References Cited

U.S. PATENT DOCUMENTS

| | | | |
|---|---|---|---|
| 4,594,443 | 6/1986 | Bianchi et al. | 560/53 |
| 4,904,675 | 2/1990 | Winter-Mihaly et al. | 514/340 |
| 4,968,817 | 11/1990 | Brima | 549/295 |

FOREIGN PATENT DOCUMENTS

| | | |
|---|---|---|
| 0010347 | 4/1980 | European Pat. Off. . |
| 0099692 | 2/1984 | European Pat. Off. . |
| 0134179 | 3/1985 | European Pat. Off. . |
| 0403891 | 12/1990 | European Pat. Off. . |
| 0436189 | 7/1991 | European Pat. Off. . |
| 5178706 | 7/1993 | Japan . |
| 9116055 | 10/1991 | WIPO . |
| 9219610 | 11/1992 | WIPO . |
| 9623773 | 8/1996 | WIPO . |

OTHER PUBLICATIONS

Stein et al., "The Discovery of Sulfonamide Endothelin Antagonists and the Development of the Orally Active ET$_A$ Antagonist 5–(Dimethylamino)–N–(3, 4–dimethyl–5–isoxazolyl)–1–naphthalenesulfonamide", *J. Med. Chem.*, 1994, 37:3, 329–331.

Foley et al., "Reversal of Subarachnoid Hemorrhage–induced Vasoconstriction with an Endothelin Receptor Anatagonist", *Neurosurgery*, 1994, 34:1, 108–113.

Rio and Hardy, "Triphényl–3,4,5 H–5 furannone–2, acide cis–benzoyl–3 diphényl–2,3 acrylique et dérivés", *Bulletin de la Société Chimique de France*, 1970, 10, 3572–3578.

Patwardhan and Bagawant, "Claisen–Stobbe Reaction of Phenylacetic Esters & Diketones", *Indian Journal of Chemistry*, 1973, 11:9, 1333–1334.

McEvoy and Allen, "6–(Substituted phenyl)–5–substituted–4,5–dihydro–3(2H)–pyridazinones. Antihypertensive Agents", *J. Med. Chem.*, 1974, 17:3, 281–286.

Dikshit et al., "Synthesis and biological activity of 2,3– and 3,4–diarylfurans and 2,3,4–triaryl–2,5–dihydrofurans", *Indian Journal of Chemistry*, 1990, 29B, 954–960.

Krapf et al., "Thermische Umwandlung der labilen 1:1–Addukte aus Diphenylcyclopropenon bzw. Diphenylcyclopropenthion und Ketenacetalen", *Chem. Ber.*, 1976, 109, 576–596.

Schmand et al., "Synthese eines 1,5–Naphthochinons; zur Struktur des Naphthazarins und zur Stabilität von Chinonen", *Liebigs Ann. Chem.*, 1976, 1560–1576.

Rohrscheidt and Fritz, "Zum Mechanismus der Aminabspaltung bei der Bildung von Pyrrolinonen aus N'–(1–Alkenyl)hydraziden and durch Brunnersche Oxindolsynthese", *Liebigs Ann. Chem.*, 1878, 680–693.

Padwa et al., "Migratory Aptitude Studies in the Photochemical Rearrangement of 2(5H)–Furanones", *J. Am. Chem. Soc.*, 1978, 100:26, 8247–8259.

Chelain et al., "Reaction of Aminocarbene Complexes of Chromium with Alkynes. 1. Formation and Rearrangement of Ketene and Nitrogen Ylide Complexes", *J. Am. Chem. Soc.*, 1992, 114, 8088–8098.

Weinberg and Miller, "Decomposition of 5–Aryl–5–(tert–butylperoxy)–3, 4–diphenyl–2(5H)–furanones", *J. Org. Chem.*, 1979, 44:25, 4722–4725.

Daroca et al., "Reactivity of Pyrrole Pigments. Part 5: Electrophilic Substitution—Nitration and Bromination–of Some Pyrromethenones and 5–Arylmethylene–3, 4–dimethyl–3–pyrrolin–2–ones", *Monatschefte für Chemie*, 1984, 115, 357–373.

Falsone and Wingen, "Synthese von 2–Oxo–5H–furanen unter Wittig–Horner Bedingungen", *Arch. Pharm.*, 1984, 317, 802–806.

Verma et al., "Smooth Conversion of 3,4–Diarylcoumarins and 3,4,5–Triaryl–2(5H)–furanones to 2H–Chromene and 2,5–Dihydrofuran Derivatives with Dimethyl Sulfide–Borane Complex", *Synthesis*, 1988, 1, 68–70.

Pratapan et al., "Substituent Effects in the Photochemistry of 5–Aryl–3,3–diphenyl–2(3H)–furanones. Steady–State and Laser Flash Photolysis Studies", *J. Org. Chem.*, 1988, 53, 5826–5831.

Krafft and Pankowski, "Butenolide synthesis using acyl cobalt complexes", *Tetrahedron Letters*, 1990, 31:36, 5139–5142.

(List continued on next page.)

*Primary Examiner*—Jane Fan
*Attorney, Agent, or Firm*—Elizabeth M. Anderson

[57] ABSTRACT

Novel small molecular biaryl compounds as inhibitors of endothelin converting enzyme are described, as well as methods for the preparation and pharmaceutical compositions of the same, which are useful in treating elevated levels of endothelin, acute and chronic renal failure, hypertension, myocardial infarction, myocardial ischemia, cerebral vasospasm, cerebral ischemia, cerebral infarction, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, stroke, benign prosthatic hyperplasia (BPH), and diabetes.

4 Claims, No Drawings

OTHER PUBLICATIONS

Alcaide and Rodríguez–López, "Reaction of N–Trimethylsilyl Benzil Monoimine with Simple Lithium Ester Enolates. A Synthetic Tool for the Regioselective One–Pot Preparation of Novel Polyfunctional Pyrrolines", *J. Chem. Soc.–Perkin Trans.*, 1990, 1, 2451–2457.

Dinulescu et al., "IX. Reaction of 1–chloro–1, 2–diphenyl–3–aryl–π–allylpalladium complexes with carbon monoxide", *Journal of Organonmetallic Chemistry*, 1977, 140, 91–96.

Chan et al., "Solvent chelation and concentration effects on the benzannulation reaction of chromium carbene complexes and acetylenes", *Journal of Organometallic Chemistry*, 1987, 334, 9–56.

Pennanen, "Studies on the furan series. Part VIII. The reaction of ynamines with acyloins. A convenient preparation of 4,5–di(2–furyl and 2–thienyl)–2(5H)–furanones and –furans", *Heterocycles*, 1977, 6:6, 701–706.

Endo and Shudo, "Anionic hertero[3,3]rearrangements. N–Acyl–N'–enylhydrazines to pyrrolidinones", *Heterocycles*, 1992, 33:1, 91–95.

Dötz et al., "LVII. Amidinocarben–Chelatkomplexe des Chroms und Molybdäns: Synthese, Struktur und Cycloadditionen mit Alkinen", *Journal of Organometallic Chemistry*, 1993, 459, 169–176.

Herndon and Zora, "Reaction of Cyclopropylcarbene–Molybdenum Complexes with Alkynes: Formation of Cycloheptadienones under Mild Conditions", *Synlett*, 1993, 5, 363–364.

Tyvorskii and Kukharev "Reaction of alkyl– and phenyl–substituted 5–aminomethyl–2(5H)–furanones with dimethylamine", *Russian Journal of Organic Chemistry*, 1993, 29:5(2), 840–843.

Clozel et al., "Pathophysiological role of endothelin revealed by the first orally active endothelin receptor antagonist", *Nature*, 1993, 365, 759–761.

Ohno, "Effects of Endothelin–specific Antibodies and Endothelin in Spontaneously Hypertensive Rats", *J. Tokyo Women's Medical College*, 1991, 61:10–11, 951–959.

Lerman et al., "Endothelin Has Biological Actions at Pathophysiological Concentrations", *Circulation*, 1991, 83:5, 1808–1814.

Rodeheffer et al., "Circulating plasma endothelin correlates with the severity of congestive heart failure in humans", *Am. J. Hypertension*, 1991, 4:9A–10A.

Arai et al., "Cloning and expression of a cDNA encoding an endothelin receptor", *Nature*, 1990, 348, 730–732.

Sakurai et al., "Cloning of a cDNA encoding a non–isopeptide–selective subtype of the endothelin receptor", *Nature*, 1990, 348, 732–735.

Lin et al., "Cloning and functional expression of a vascular smooth muscle endothelin 1 receptor", *Proc. Natl. Acad. Sci. USA*, 1991, 88, 3185–3189.

Sakamoto et al., "Cloning and functional expression of human cDNA for the $ET_B$ endothelin receptor", *Biochem. Biophys. Res. Chem.*, 1991, 178:2, 656–663.

Hosoda et al., "Cloning and expression of human endothelin–1 receptor cDNA", *FEBS Lett.*, 1991, 287:1,2; 23–26.

Takayanagi et al., "Presence of non–selective type of endothelin receptor on vascular endothelium and its linkage to vasodilation", *FEBS Lett.*, 1991, 282:1, 103–106.

Panek et al., "Endothelin and structurally related analogs distinguish between endothelin receptor subtypes", *Biochem. Biophys. Res. Chem.*, 1992, 183:2, 566–571.

Saeki et al., "[$Ala^{1,3,11,15}$]Endothelin–1 analogs with $ET_B$ agonistic activity", *Biochem. Biophys. Res. Chem.*, 1991, 179:1, 286–292.

Nakagawa et al., "Measurement of Immunoreactive Endothelin–1 in Plasma of a Patient with Malignant Hemangioendothelioma", *Nippon Hifuka Gakkai Zasshi*, 1990, 100, 1453–1456.

Norguchi et al., "An Endothelin $(ET)_A$ Receptor Antagonists, BQ–123, Blocks ET–1 Induced Bronchoconstriction and Tracheal Smooth Muscle (TSM) Contraction in Allergic Sheep", *Am. Rev. Respir. Dis.*, 1992, 145 (4 Part 2), A858.

Clark et al., "Plasma endothelin levels in preeclampsia: Elevation and correlation with uric acid levels and renal impairment", *Am. J. Obstet Gynecol.*, 1992, 166:3, 962–968.

Pittet et al., "Elevated Plasma Endothelin–1 Concentrations Are Associated with the Severity of Illness in Patients with Sepsis", *Ann. Surg.*, 1991, 213:3, 261–264.

Gandhi et al., "Endothelin, a Potent Peptide Agonist in the Liver", *J. Biol. Chem.*, 1990, 265:29, 17432–17435.

Kanno et al., "Endothelin–1 and Vasculitis", *J. Amer. Med. Assoc.*, 1990, 264:22, 2868.

Zamora et al., "Serum endothelin–1 concentrations and cold provocation in primary Raynaud's phenomenon", *Lancet*, 1990, 336, 1144–1147.

Tahara et al., "Circulating Immunoreactive Endothelin in Patients Undergoing Percutaneous Transluminal Coronary Angioplasty", *Metabolism*, 1991, 40:12, 1235–1237.

Stewart et al., "Increased Plasma Endothelin–1 in Pulmonary Hypertension: Marker or Mediator of Disease?", *Annals of Internal Medicine*, 1991, 114:6, 464–469.

Yasuda et al., "Circulating immunoreactive endothelin in ischemic heart disease", *American Heart Journal*, 1990, 119:4, 801–806.

Stewart et al., "Plasma endothelin in coronary venous blood from patients with either stable or unstable angina", *Br. Heart J.*, 1991, 66, 7–9.

López–Farré et al., "A role for endothelin in the maintenance of post–ischaemic renal failure in the rat", *Journal of Physiology*, 1991, 444, 513–522.

Stockenhuber et al., "Plasma levels of endothelin in chronic renal failure and after renal transplantation: impact on hypertension and cyclosporin A–associated nephrotoxicity", *Clinical Science*, 1992, 82, 255–258.

Miura et al., "Ischemic Bowel Necrosis Induced by Endothelin–1: An Experimental Model in Rats", *Digestion*, 1991, 48, 162–172.

Masuda et al., "Effect of intravascular ethanol on modulation of gastric mucosal integrity: possible role of endothelin–1", *Am. J. Physiol.*, 1992, 262, G785–G790.

Murch et al., "High endothelin–1 immunoreactivity in Crohn's disease and ulcerative colitis", *Lancet*, 1992, 339, 381–384.

Clozel and Watanabe, "BQ–123, A Peptidic Endothelin $ET_A$ Receptor Antagonist, Prevents the Early Cerebral Vasospasm Following Subarachnoid Hemorrhage After Intracisternal but not Intravenous Injection", *Life Sciences*, 1993, 52:9, 825–834.

Basil et al., "Hemodynamic effects of an endothelin (ET) receptor antagonist in three rat models of hypertension", *J. Hypertension*, 1992, 10(Suppl 4), S49.

Han et al., "Cardiac and vascular actions of sarafotoxin S6b and endothelin–1", *Life Sciences*, 1990, 46:11, 767–775.

Allen and Frame, "The condensation of certain γ–ketonic esters with aromatic aldehydes", *Can. J. Research*, 1932, 6, 605–613.

Allen et al., "The condensation of certain γ–ketonic esters with aromatic aldehydes. II", *Can. J. Research*, 1933, 8, 137–141.

Canévet and Graff, "Réactions de Friedel–Crafts de dérivés aromatiques sur des composés dicarbonylés–1,4 éthyléniques–2,3.II Alkylations par quelques hydroxy–5 ou chloro–5 hydro–2,5 furannones–2. Nouvelle méthode de synthése des acids 1H–indénecarboxyliques–1", *Tetrahedron*, 1978, 34, 1935–1942.

Mise et al., "Rhodium Carbonyl Catalyzed Carbonylation of Unsaturated Compounds. 2. Synthesis of 5–Alkoxy–2(5H)–furanones by the Carbonylation of Acetylenes in Alcohol", *J. Org. Chem.*, 1983, 48, 238–242.

Anselmi et al., "A One–Step Conversion of N–Acylaminoketones into 5–Alkylidene–3 pyrrolin–2–ones", *J. Heterocyclic Chem.*, 1983, 20, 687–689.

Yoshida et al., "Cycloaddition of Diphenylcyclopropenone with Carboximidate, Carboximidamide, and Carboximidothioate", *Bull. Chem. Soc. Jpn.*, 1983, 56, 3849–3850.

Watanabe et al., "Endothelin in myocardial infarction", *Nature*, 1990, 344, 114.

Margulies et al., "Increased Endothelin in Experimental Heart Failure", *Circulation*, 1990, 82:6, 2226–2230.

Kon et al., "Glomerular Actions of Endothelin In Vivo", *J. Clin. Invest.*, 1989, 83, 1762–1767.

Perico et al., "Endothelin Mediates the Renal Vasoconstriction Induced by Cyclosporine in the Rat", *J. Am. Soc. Nephrol.*, 1990, 1:1, 76–83.

Koshi et al., "Inhibition of Endothelin (ET)–1– and ET–2–Induced Vasoconstriction by Anti–ET–1 Monoclonal Antibody", *Chem. Pharm. Bull.*, 1991, 39:5, 1295–1297.

Miyamori et al., "Systemic and regional effects of endothelin in rabbits: effects of endothelin antibody", *Clin. Exp. Pharmacol. Physiol.*, 1990, 17, 691–696.

Collier et al., "Plasma Endothelinlike Immunoreactivity Levels in IDDM Patients With Microalbuminuria", *Diabetes Care*, 1992, 15:8, 1038–1040.

Nikolov and Semkova, "Cerebrovascular and CNS Effects of Endothelins—Target for Pharmacological Modification?", *Drugs of Today*, 1992, 28:5, 303–310.

Lerman et al., "Circulating and tissue endothelin immunoreactivity in advanced atherosclerosis", *New England J. Med.*, 1991, 325:14, 997–1001.

Rovero et al., "Structure–activity studies on endothelin (16–21), the C–terminal hexapeptide of the endothelins, in the guinea–pig bronchus", *Br. J. Pharmacol.*, 1990, 101, 232–234.

Clozel et al., "The discovery of Ro 46–2005, an orally avilable non–peptide antagonist of $ET_A$ and $ET_B$ receptors", *Third Intl. Conf. on Endothelin*, Abstract Book, Feb. 5–17, 1993 p. 17.

Doherty et al., "Design of C–terminal peptide antagonists of endothelin: structure–activity relationships of ET–1[16–21, D–His$^{16}$]", *Bioorg. & Med. Chem. Lett.*, 1990, 3:4, 497–502.

Allen et al., "The condensation of certain γ–ketonic esters with aromatic aldehydes", *Can. J. Research*, 1934, 11, 382–394.

Allen et al., "α–Aryl–β–aroylpropionic acids and their condensation products with aromatic aldehydes", *Can. J. Chem.*, 1956, 34, 926–930.

CA 122: 81200 Masatoshi et al., 1995.
CA 121:9391, Masatoshi et al., 1994.
CA 118:19726, Masatoshi et al., 1993.
CA 123:33440, Yoshimura et al., 1995.
CA 109:230819, Winter–Mihaly et al., 1988.
CA 105:226539, Nakagawa et al., 1986.
CA 104 :224890, Juraszyk et al., 1986.
CA 101: 21159, Lesher et al., 1984.

SMALL MOLECULE BIARYL COMPOUNDS AS INHIBITORS OF ENDOTHELIN CONVERTING ENZYME

BACKGROUND OF THE INVENTION

This application claims the benefit of U.S. Provisional application Ser. No. 60/028,803 filed Oct. 29, 1996.

The present invention relates to novel biaryl inhibitors of endothelin converting enzyme useful as pharmaceutical agents, to methods for their production, to pharmaceutical compositions which include these compounds and a pharmaceutically acceptable carrier, and to pharmaceutical methods of treatment. More particularly, the novel compounds of the present invention are inhibitors of endothelin converting enzyme useful in treating elevated levels of endothelin and in controlling hypertension, myocardial infarction and ischemia, metabolic, endocrinological, and neurological disorders, congestive heart failure, endotoxic and hemorrhagic shock, septic shock, subarachnoid hemorrhage, arrhythmias, asthma, acute and chronic renal failure, cyclosporin-A induced nephrotoxicity, angina, gastric mucosal damage, ischemic bowel disease, cancer, pulmonary hypertension, preeclampsia, atherosclerotic disorders including Raynaud's disease and restenosis, cerebral ischemia and vasospasm, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogs with incorrect disulfide pairings exhibit at least 100-fold less vasoconstrictor activity.

Endothelin-1 is generated from a 203 amino acid peptide known as preproendothelin by an unknown dibasic endopeptidase. This enzyme cleaves the prepropeptide to a 38 (human) or 39 (porcine) amino acid peptide known as big endothelin or proendothelin. Big ET is then cleaved by an enzyme, known as endothelin converting enzyme or ECE, to afford the biologically active molecule ET-1. Big ET is only 1% as potent as ET-1 in inducing contractile activity in vascular strips but it is equally potent in vivo at raising blood pressure, presumably by rapid conversion to ET-1 (Kimura S, Kasuya Y, Sawamura T, et al., "Conversion of big endothelin-1 to 21-residue endothelin-1 is essential for expression of full vasoconstrictor activity: Structure-activity relationship of big endothelin-1," *J Cardiovasc Pharmacol* 1989;13:S5).

Endothelin converting enzyme (ECE) is a metalloprotease that was recently cloned by Yanagisawa, et al., (*Cell* 1994; (78):473–485). The ECE-1 enzyme has two isoforms which differ only in their N-terminus and their cellular location. In vitro both enzymes display, within experimental error, identicle activities (FEBS Letters 1995; (371) 140–144). The ECE gene has more recently been expressed in human tissues (*Biochem Biophys Res Comm* 1995; (211):249–253). A review article summarizes the molecular pharmacology of the ECE enzymes (*Biochem Pharm* 1996; (51):91–102).

Micromolar concentrations of phosphoramidon have been shown to block the pressor response of big ET both in vitro and in vivo (Takada J, supra; Fukuroda T, Noguchi K, Tsuchida S, et al., "Inhibition of biological actions of big endothelin-1 by phosphoramidon," *Biochem Biophys Res Commun* 1990;172:390; Matsumura Y, Hisaki K, Takaoka M, Morimoto S, "Phosphoramidon, a metalloproteinase inhibitor, suppresses the hypertensive effect of big endothelin-1," *Eur J Pharmacol* 1990;185:103; McMahon E G, Palomo M A, Moore W M, et al., "Phosphoramidon blocks the pressor activity of porcine big endothelin-1-(1-39) in vivo and conversion of big endothelin-1-(1-39) to endothelin-1-(1-21) in vitro," *Proc Natl Acad Sci USA* 1991;88:703). It has recently been reported that phosphoramidon is able to inhibit vasoconstrictor effects evoked by intravenous injections of big ET-1 in anaesthetized pigs, but did not have any effect on the plasma ET-1 level (Modin A, Pernow J, Lundberg J M, "Phosphoramidon inhibits the vasoconstrictor effects evoked by big endothelin-1 but not the elevation of plasma endothelin-1 in vivo," *Life Sci* 1991;49:1619). It should be noted that phosphoramidon is a rather general metalloproteinase inhibitor and clearly the discovery of specific ECE inhibitors such as those described in the present invention is important.

The importance of ECE inhibitors is supported further by more recent reports. Several studies demonstrating the inhibition of ECE by metalloprotease inhibitors like phosphoramidon in vitro have been published (Doherty A. D., Endothelin: A New Challenge. *J Med Chem* 1992;35:1493; Simonson J. S., Endothelins: Multifunctional Renal Peptides. *Physiological Reviews*, 1993;73:375; Opgenorth T. J.; Wu-Wong J. R.; Shiosaki K. Endothelin Converting Enzymes, *FASEB J* 1992;6:2653–2659; Pollock D. M.; Opgenorth T. J. Evidence for metalloprotease involvement in the in vivo effects of big endothelin-1 *Am J Physiol* 1991;261:257–263). These studies have also been followed up by in vivo studies where the effects of ET in physiological conditions have been blocked by ECE inhibitors. For example, several reports have demonstrated that phosphoramidon ($IC_{50}=~1$ $\mu$M) inhibits ECE in vitro. These results were supported by in vivo studies where phosphoramidon blocked the vasoconstrictive effects of ET. In ganglion-blocked anesthetized rats the pressor response of big ET-1 was blocked by phosphoramidon in a dose-dependent manner (McMahon E. G.; Palomo M. A.; Moore W. M. Phosphoramidon blocks the pressor activity of big endothelin (1-39) and lowers blood pressure in spontaneously hypertensive rats. *J Cardiovasc Pharmacol* 1991;17(Suppl. 17):S29–S33; McMahon E. G.; Palomo M. A.; Moore W. M.; McDonald J. F.; Stern M. K. Phosphoramidon blocks the pressor activity of porcine big endothelin-1-(1-39) in vivo and conversion of big endothelin-1-(1-39) to endothelin-1-(1-21) in vitro *Proc Natl Acad Sci (USA)* 1991;88:703–707). Phosphoramidon was also shown to inhibit the effects of big ET-1 in the microvasculature of anesthetized hamsters and has also been used to suppress the lethality induced by the intravenous infusion of big ET-1 (Lawerence E.; Brain S. D. Big endothelin-1 and big endothelin-3 are constrictor agents in the microvasculature: evidence for the local phosphoramidon-sensitive conversion of big endothelin-1. *Eur J Pharmacol* 1993;233:243–250). In all cases it was shown that phosphoramidon inhibited the effects of big ET-1 and not ET-1 indicating that it was not behaving as a receptor antagonist. Intracisternal administration of big ET-1 in anesthetized dogs decreased the caliber of the basilar artery on the angiogram and systemic arterial pressure was also elevated. These effects were blocked by phosphoramidon (Shinyama H; Uchida T; Kido H; Hayashi K; Watanabe M; Matsumura Y; Ikegawa R; Takaoka M; Morimoto S. Phosphoramidon inhibits the conversion of intracisternally administered big endothelin-1 to endothelin-1. *Biochem Biophys Res Commun* 1991;178:24–30). Similar enzyme inhibitory activity has been reported in the studies involving phosphoramidon sensitive inhibition of hemodynamic actions of big ET-1 in rat brain (Hashim M. A.; Tadepalli. Functional evidence for the presence of a phosphoramidon-sensitive enzyme in rat brain that converts big endothelin-1 to endothelin-1. *Life Sci* 1991;49:207–211).

The blockade of ECE with phosphoramidon has further been shown to reduce elevated pulmonary vascular resistance after cardiopulmonary bypass in young piglets, a model for pulmonary hypertension (*Surgery*, 1995;118:440–445).

A peptide derivative containing a D-Val residue, [D-Val$^{22}$]Big ET-1{16–38}, has been reported that inhibits ECE (*FEBS Lett* 1994;353:84–88). This analog was shown to inhibit the ET-1 induced release of dopamine from the stratum of rats. A dose of 0.33 pmol caused a 50% reduction of response.

A series of amino acid derivatives containing a phosphonic acid group have been reported as ECE and neutral endopeptidase (NEP) inhibitors (*Biochem Biophys Res Comm* 1994;204:407–412). One of these analogs, CGS 26303, was shown to be effective at lowering the antihypertensive responses in the SHR after an IV infusion.

A series of phosphinic acid derivatives have been reported as inhibitors of ECE (*Bioorgan Med Chem Lett* 1996;6:1257–1260). These analogs were shown to be selective for ECE over the closely related enzyme NEP.

Endothelin is involved in many human disease states.

Several in vivo studies with ET antibodies have been reported in disease models. Left coronary artery ligation and reperfusion to induce myocardial infarction in the rat heart, caused a four- to seven-fold increase in endogenous endothelin levels. Administration of ET antibody was reported to reduce the size of the infarction in a dose-dependent manner (Watanabe T, et al., "Endothelin in Myocardial Infarction," *Nature* (Lond.) 1990;344:114). Thus, ET may be involved in the pathogenesis of congestive heart failure and myocardial ischemia (Margulies K B, et al., "Increased Endothelin in Experimental Heart Failure," *Circulation* 1990;82:2226).

Studies by Kon and colleagues using anti-ET antibodies in an ischemic kidney model, to deactivate endogenous ET, indicated the peptide's involvement in acute renal ischemic injury (Kon V, et al., "Glomerular Actions of Endothelin In vivo," *J Clin Invest* 1989;83:1762). In isolated kidneys, preexposed to specific antiendothelin antibody and then challenged with cyclosporine, the renal perfusate flow and glomerular filtration rate increased, while renal resistance decreased as compared with isolated kidneys pre-exposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N, et al., "Endothelin Mediates the Renal Vasoconstriction Induced by Cyclosporine in the Rat," *J Am Soc Nephrol* 1990;1:76).

Others have reported inhibition of ET-1 or ET-2-induced vasoconstriction in rat isolated thoracic aorta using a monoclonal antibody to ET-1 (Koshi T, et al., "Inhibition of Endothelin (ET)-1 and ET-2-Induced Vasoconstriction by Anti-ET-1 Monoclonal Antibody," *Chem Pharm Bull* 1991;39:1295).

Combined administration of ET-1 and ET-1 antibody to rabbits showed significant inhibition of the blood pressure and renal blood flow responses (Miyamori I, et al., Systemic and Regional Effects of Endothelin in Rabbits: Effects of Endothelin Antibody," *Clin Exp Pharmacol Physiol* 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY), there were no significant changes in these parameters (Ohno A, "Effects of Endothelin-Specific Antibodies and Endothelin in Spontaneously Hypertensive Rats," *J Tokyo Women's Med Coll* 1991;61:951).

Burnett and co-workers recently demonstrated that exogenous infusion of ET (2.5 ng/kg/mL) to anesthetized dogs, producing a doubling of the circulating concentration, did have biological actions (Lerman A, et al., "Endothelin Has Biological Actions at Pathophysiological Concentrations," *Circulation* 25 1991;83:1808). Thus heart rate and cardiac output decreased in association with increased renal and systemic vascular resistances and antinatriuresis. These studies support a role for endothelin in the regulation of cardiovascular, renal, and endocrine function.

In the anesthetized dog with congestive heart failure, a significant two- to three-fold elevation of circulating ET levels has been reported (Cavero PG, et al., "Endothelin in Experimental Congestive Heart Failure in the Anesthetized Dog," *Am J Physiol* 1990;259:F312), and studies in humans have shown similar increases (Rodeheffer R J, et al., "Circulating Plasma Endothelin Correlates With the Severity of Congestive Heart Failure in Humans," *Am J Hypertension* 1991;4:9A). When ET was chronically infused into male rats, to determine whether a long-term increase in circulating ET levels would cause a sustained elevation in mean arterial blood pressure, significant, sustained, and dose-dependent increases in mean arterial blood pressure were observed. Similar results were observed with ET-3 although larger doses were required (Mortenson L H, et al., "Chronic Hypertension Produced by Infusion of Endothelin in Rats," *Hypertension* 1990;15:729). Recently the nonpeptide endothelin antagonist RO 46-2005 has been reported to be effective in models of acute renal ischemia and subarachnoid hemorrhage in rats (3rd International Conference on Endothelin, Houston, Tex., February 1993). In addition, the $ET_A$ antagonist BQ-153 has also been shown to prevent early cerebral vasospasm following subarachnoid hemorrhage after intracisternal injection (Clozel M., et al., *Life Sciences* 1993;52:825); to prevent blood pressure increases in stroke-prone spontaneously hypertensive rats (Nishikibe M, et al., *Life Sciences* 1993;52:717); and to attenuate the renal vascular effects of ET-1 in anaesthetized pigs (Cirino M, et al., *J Pharm Pharmacol* 1992;44:782).

Plasma endothelin-1 levels were dramatically increased in a patient with malignant hemangio-endothelioma (Nakagawa K, et al., *Nippon Hifuka Gakkai Zasshi* 1990;100:1453).

The ET receptor antagonist BQ-123 has been shown to block ET-1-induced bronchoconstriction and tracheal smooth muscle contraction in allergic sheep providing evidence for expected efficacy in bronchopulmonary diseases such as asthma (Noguchi, et al., *Am Rev Respir Dis* 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B A, et al., *Am J Obstet Gynecol* 1992;166:962).

Plasma immunoreactive endothelin-1 concentrations are elevated in patients with sepsis and correlate with the degree of illness and depression of cardiac output (Pittett J, et al., *Ann Surg* 1991;213(3):261).

In addition, the ET-1 antagonist BQ-123 has been evaluated in a mouse model of endotoxic shock. This $ET_A$ antagonist significantly increased the survival rate in this model (Toshiaki M, et al., 20.12.90. EP 0 436 189 A1).

Endothelin is a potent agonist in the liver eliciting both sustained vasoconstriction of the hepatic vasculature and a significant increase in hepatic glucose output (Gandhi C B, et al., *J Biol Chem* 1990;265(29):17432). In streptozotocin-diabetic rats, there is an increased sensitivity to endothelin-1 (Tammesild P J, et al., *Clin Exp Pharmacol Physiol* 1992;19(4):261). In addition, increased levels of plasma ET-1 have been observed in microalbuminuric insulin-dependent diabetes mellitus patients indicating a role for ET in endocrine disorders such as diabetes (Collier A, et al., *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil M K, et al., *J Hypertension* 1992;10(Suppl 4):S49). The endothelins have been shown to be arrhythmogenic, and to have positive chronotropic and inotropic effects, thus ET receptor blockade would be expected to be useful in arrhythmia and other cardiovascular disorders (Han S-P, et al., *Life Sci* 1990;46:767).

The widespread localization of the endothelins and their receptors in the central nervous system and cerebrovascular circulation has been described (Nikolov R K, et al., *Drugs of Today* 1992;28(5):303). Intracerebroventricular administration of ET-1 in rats has been shown to evoke behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1-induced lesion development in a new model of local ischemia in the brain has been described.

Circulating and tissue endothelin immunoreactivity is increased more than twofold in patients with advanced atherosclerosis (Lerman A., et al., *New England J Med* 1991;325:997). Increased endothelin immunoreactivity has also been associated with Buerger's disease (Kanno K, et al., *J Amer Med Assoc* 1990;264 2868) and Raynaud's phenomenon (Zamora M R, et al., *Lancet* 1990;336:1144). Likewise, increased endothelin concentrations were observed in hypercholesterolemic rats (Horio T, et al., *Atherosclerosis* 1991;89:239).

An increase of circulating endothelin levels was observed in patients that underwent percutaneous transluminal coronary angioplasty (PTCA) (Tahara A, et al., *Metab Clin Exp* 1991;40:1235; Sanjay K, et al., *Circulation* 1991;84(Suppl. 4):726).

Increased plasma levels of endothelin have been measured in rats (Stelzner T J, et al., *Am J Physiol* 1992;262:L614) and humans (Miyauchi T, et al., *Jpn J Pharmacol* 1992;58:279P; Stewart D J, et al., *Ann Internal Medicine* 1991;114:464) with pulmonary hypertension.

Elevated levels of endothelin have also been measured in patients suffering form ischemic heart disease (Yasuda M, et al., *Amer Heart J* 1990;119:801; Ray S G, et al., *Br Heart J* 1992;67:383) and either stable or unstable angina (Stewart J T, et al., *Br Heart J* 1991;66:7).

Infusion of an endothelin antibody 1 hour prior to and 1 hour after a 60-minute period of renal ischemia resulting in changes in renal function versus control. In addition, an increase in glomerular platelet-activating factor was attributed to endothelin (Lopez-Farre A, et al., *J Physiology* 1991;444:513). In patients with chronic renal failure as well as in patients on regular hemodialysis treatment mean plasma endothelin levels were significantly increased (Stockenhuber F, et al., *Clin Sci* (Lond.) 1992;82:255). In addition, it has been suggested that the proliferative effect of endothelin on mesangial cells may be a contributing factor in chronic renal failure (Schultz P J, *J Lab Clin Med* 1992;119:448).

Also, Haleen, S., et al., *FASEB J* April 1994, demonstrated efficacy of an $ET_A/ET_B$ antagonist, PD 145065, which essentially also blocks all ET function (similar to an ECE inhibitor) in a severe model of acute renal failure.

The effects of endothelin receptor blockade on ischemia-induced acute renal failure and mortality were assessed in rats undergoing unilateral nephrectomy and global ischemia in the remaining kidney. Sprague Dawley male rats (300–400 g) were housed in metabolic cages for 2 days before and 7 days after renal injury; urine output and plasma creatinine levels were monitored daily. On the day of renal injury, rats were anesthetized with sodium pentobarbital (50 mg/kg, IP), heparinized (50 units, IV), and instrumented with a tail vein canulae for drug or vehicle infusion. Both kidneys were exposed via a flank incision and the right kidney was removed. The left renal artery was clamped for 60 minutes and released. PD 145065 was infused 60 minutes prior to and following the ischemic period. Renal injury was evident 1 and 2 days following ischemia from a tenfold increase in plasma creatinine levels and significant decreases in urine output. Mortality occurred primarily between the second and third days postinjury. However, mortality was significantly less (52%, N=23) in rats treated with PD 145065 compared to vehicle rats (83%, N=23). In addition, urine output on the second day following renal injury was significantly different between treatment groups on either the first or second days postinjury. Thus blockade of endothelin receptors with PD 145065 significantly decreases mortality in rats subjected to ischemia-induced renal failure.

Local intra-arterial administration of endothelin has been shown to induce small intestinal mucosal damage in rats in a dose-dependent manner (Mirua S, et al., *Digestion* 1991;48:163). Administration of endothelin-1 in the range of 50 to 500 pmol/kg into the left gastric artery increased the tissue type plasminogen activator release and platelet activating formation and induced gastric mucosal hemorrhagic change in a dose-dependent manner (Kurose I, et al., *Gut* 1992;33:868). Furthermore, it has been shown that an anti-ET-1 antibody reduced ethanol-induced vasoconstriction in a concentration-dependent manner (Masuda E, et al., *Am J Physiol* 1992;262:G785). Elevated endothelin levels have been observed in patients suffering from Crohn's disease and ulcerative colitis (Murch S R, et al., *Lancet* 1992;339:381).

Additionally, there is a correlation between the inhibition of ECE in an in vitro assay, as used and described for the quinazolines of the present invention, and demonstration of in vivo activity in various pathophysiological conditions. For example, Grover G. J., et al., *J Pharmacol Exp Ther* 1992;263:1074–1082, tested the effect of phosphoramidon, an ECE inhibitor, in a rat model of ischemia. Thus, Grover G. J., et al. determined the effect of endothelin-1 (ET-1) and big ET-1 on coronary flow and contractile function in isolated nonischemic and ischemic rat hearts. Both ET-1 ($IC_{50}$=12 pMol) and big ET-1 ($IC_{50}$=2 nMol) reduced coronary flow in a concentration-dependent manner. Both 30 pMol ET-1 and 10 nMol big ET-1 pretreatment significantly reduced the time to contracture in globally ischemic rat hearts,suggesting a preischemic effect. Phosphoramidon ($IC_{50}$=100 $\mu$M) and BQ-123 (0.3 $\mu$M, $ET_A$ receptor antagonist) abolished the preischemic increase in coronary perfusion pressure induced by big ET-1 as well as its preischemic effect. Phosphoramidon was also given IV to rats subjected to coronary occlusion and reperfusion and was found to significantly reduce infarct size 24 hour postischemia. Phosphoramidon has been disclosed to be an effective inhibitor of ECE, $IC_{50}$=1 $\mu$M, (European Published Patent Application EP 0518299 A2 and International Published Patent Application WO 92/13944).

Two natural product isolates, WS75624A and WS75624B, have been identified and published *J Antibiotics* 1995;48(10):1066 and *J Antibiotics* 1995;48(10):1073.

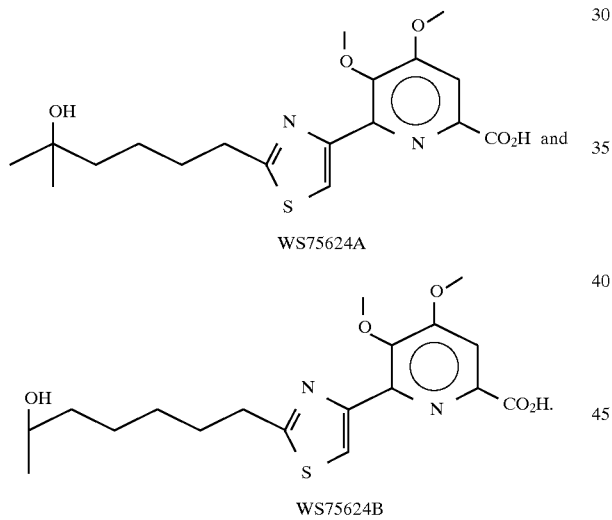

WS75624A

WS75624B

These derivatives as well as two additional natural product isolates of undetermined structure, have been disclosed as inhibitors of endothelin converting enzyme, GB 2272435A.

SUMMARY OF THE INVENTION

The present invention is a compound of Formula I,

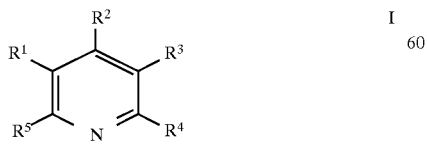

or a pharmaceutically acceptable salt thereof, wherein
$R^1$, $R^2$, and $R^3$ are each independently selected from hydrogen;

halogen;

alkyl which is straight, or cyclic unsubstituted or substituted by from 1 to 4 substituents each independently selected from halogen, amino, monoalkylamino, dialkylamino, hydroxy, alkoxy, nitro, aryl, cyano, or carboxyl;

alkoxy;

monoalkylamino;

dialkylamino;

nitro;

cyano;

hydroxy;

carboxyl;

carboxamide;

monoalkylcarboxamide;

dialkylcarboxamide;

thioalkyl;

thiol; and sulfonic acid.

$R^4$ is

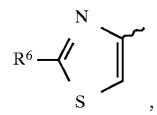

wherein $R^6$ is hydrogen;
straight or branched alkyl which is unsubstituted or substituted with from 1 to 4 substituents each independently selected from halogen, amino, monoalkylamino, dialkylamino, nitro, cyano, aryl, hydroxyl, alkoxy, and carboxyl; and wherein $R^6$ is amino, monoalkylamino, dialkylamino, or halogen;

$R^4$ is also

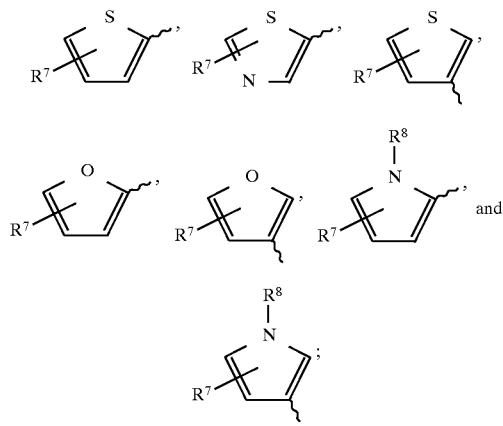

where $R^7$ is hydrogen or alkyl of from 1 to 4 carbon atoms which alkyl is unsubstituted or substituted by from 1 to 4 substituents each independently selected from halogen, amino, thiol, monoalkylamino, dialkylamino, nitro, cyano, hydroxy, alkoxy, carboxyl, aryl or sulfonic acid;

$R^8$ is alkyl straight or branched; and $R^5$ is $CO_2H$; $CH_2OH$; or

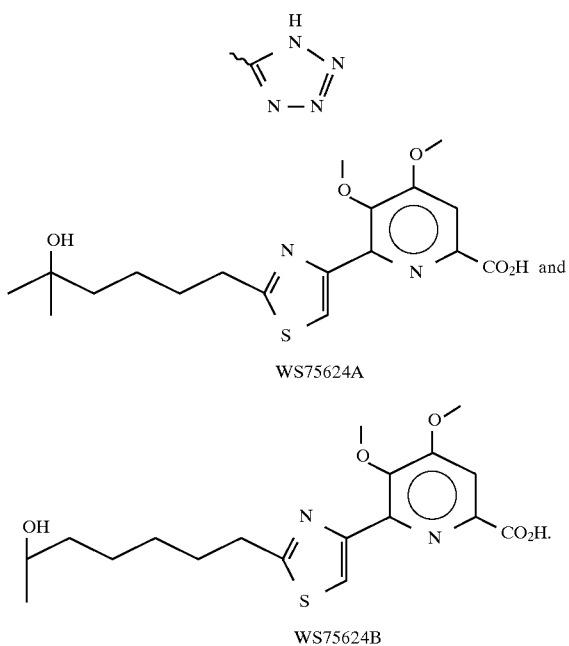

WS75624A

WS75624B

Preferred compound of the present invention are:
6-(2-Methyl-thiazol-4-yl)-4,5-dimethoxy-pyridine-2-carboxylic acid,
6-(2-Heptyl-thiazol-4-yl)-4,5-dimethoxy-pyridine-2-carboxylic acid,
6-(2-Amino-thiazol-4-yl)-4,5-dimethoxy-pyridine-2-carboxylic acid,
6-(2-N-Methylamino-thiazol-4-yl)-4,5-dime-thoxy-pyridine-2-carboxylic acid, and
6-(Thiazol-4-yl)-4,5-dimethoxy-pyridine-2-carboxylic acid.

These ECE inhibitors can be used to treat various diseases such as; elevated levels of endothelin, acute said chronic renal failure, hypertension, myocardial infarction, myocardial ischemia, cerebral vasospasm, cerebral ischemia, cerebral infarction, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, stroke, benign prosthatic hyperplasia (BPH), and diabetes.

A third aspect of the present invention is a pharmaceutical composition for administering an effective amount of a compound of Formula I in admixture with a pharmaceutically acceptable carrier in the treatment methods mentioned above in unit dosage form.

A fourth aspect of the present invention is a novel process for the preparation of compounds of Formula I.

A fifth aspect is novel intermediates useful in the preparation of the final products.

DETAILED DESCRIPTION OF THE INVENTION

In the compounds of the present invention, the term alkyl, in general and unless specifically limited, means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like. The term alkyl also has the same meaning when used as a suffix for aminoalkyl, monoalkylamino, and dialkylamino.

The term "alkoxy" is O-alkyl as defined above for alkyl or lower alkyl.

The term "aryl" means an aromatic radical which is a phenyl group, a naphthyl group, a biphenyl group, a pyrenyl group, an anthracenyl group, or a fluorenyl group and the like, unsubstituted or substituted by 1 to 4 substituents selected from alkyl as defined above, alkoxy as defined above, trifluoromethyl, nitro, halogen, CN, $SO_3H$, $SO_2NH_2$, $SO_2CH_3$, COOH, $CONH_2$, CO-alkyl, $NH_2$, monoalkylamino, di-alkylamino.

Halogen is fluorine, chlorine, bromine, or iodine.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mande late, benz oate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S M, et al., "Pharmaceutical Salts," *J of Pharma Sci*, 1977;66:1).

The acid addition salts of said basic compounds are prepared by contacting the free base form with a sufficient amount of the desired acid to produce the salt in the conventional manner. Preferably, a compound of Formula I can be converted to an acidic salt by treating with an aqueous solution of the desired acid, such that the resulting pH is less than 4. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S M, et al., "Pharmaceutical Salts," *J of Pharma Sci* 1977;66:1).

The compounds of the present invention are valuable inhibitors of endothelin converting enzyme. The tests employed demonstrate that such compounds possess inhibitory activity towards an endothelin converting enzyme.

ASSAY CONDITIONS
Cell Culture and Preparation of Membrane Fractions
Stable transfectant CHO cells were cultured in monolayers in HamF-12 and DMEM (1:1 mixture) medium supplemented with 10% fetal bovine serum and 1 mg/mL G418. All cells were grown in a humidified incubator at 37° C. in an atmosphere of 5% CO2/95% air. The membrane fractions from CHO cells were prepared as described in (*Cell* 1994; (78):473–485).
ECE-1 Assay
For determination of $IC_{50}$ values, the reaction mixture (100 $\mu$l) contained 0.1 $\mu$M big ET-1, 100 mM Herpes-KOH (pH 7.0), 50 mM NaCl, 50 $\mu$M pepstatin A, 100 $\mu$M leupeptin, 200 $\mu$M phenylmethylsulfonyl fluoride, the indicated concentration of the inhibitor (DMSO for control), and the solubilized membrane fraction of CHO/human ECE-1 cells. The final concentration of DMSO was 1.5%. After incubation for 1 hour at 37° C. the reaction was stopped by adding EDTA to give a final concentration of 5 mM. This final mixture was then directly analyzed for the amount of ET-1 by enzyme-linked immunosorbant assay (Elisa).

Representative ECE inhibition data for compounds of Formula I are shown in Table I.

TABLE I

| Biological Activity of Compounds of the Present Invention | |
|---|---|
| Example | $IC_{50}$ ($\mu$M) |
| 1 | 1.3 |
| 2 | 1.9 |
| 3 | 1.3 |
| 4 | 1–5 |
| 5 | 1–5 |
| 6 | 5–10 |

The compounds of the present invention may be prepared generally as shown in Schemes I to III.

In Scheme I kojic acid, i, is converted to a benzyl protected derivatives, ii, with benzyl halide and base such as sodium methoxide. The hydroxy methyl group of ii is then oxidized to a carboxylic acid, iii, with an oxidizing reagent such as Jones reagent. The pyrone, iii, is then converted to a pyridone, iv, with concentrated ammonium hydroxide or ammonia. This is then reacted with diazomethane or trimethylsilyl-diazomethane in a methanolic solvent to give the trisubstituted pyridine, v. The benzyl group is then cleaved by hydrogenolysis with Pd/C and hydrogen gas to give the phenol, vi. The phenol is then subjected to a radical acylation using acetaldehyde, iron sulfate, t-butylperoxide, and sulfuric acid to give vii. The phenol is then converted to an alkoxy group with an alkyl halide and a base or diazomethane (or trimethylsilyldiazomethane) to give viii. The acetyl group is then brominated with pyridinium bromide perbromide or NBS to give ix. This alpha bromoketone can then be cyclized with a thioamide, such as x, to give the penultimate compound xi. Hydrolysis of the ester gives the acid, xii, which is a compound of Formula I.

In Scheme II the 2,6-dibromopyridine, a, is reacted with n-butyl lithium at cold temperature and then $CO_2$ to give the acid, b. The acid group of b is then converted to the ester with an alkyl halide and a base or trimethylsilyldiazomethane (or diazomethane) giving c. This is then reacted with 1-ethoxyvinyl tributyltin and bis(triphenyl phosphine) palladium(II) chloride to give the vinyl pyridine, d. This is then treated with NBS to give the alpha bromoacetyl derivative, e, which is converted to a derivative of Formula I in the same manner as ix in Scheme I.

In Scheme III compound c is coupled to a 5-membered heteroaryl bromide or boronic acid, such as 2-bromothiophene, or 3-thiophene boronic acid using various transition metal coupling reagents such as tributyltin, a Pd(0) species and/or a Pd(II) compound. This gives an ester represented by f, which can be hydrolyzed with hydroxide to give a compound of Formula I.

SCHEME I

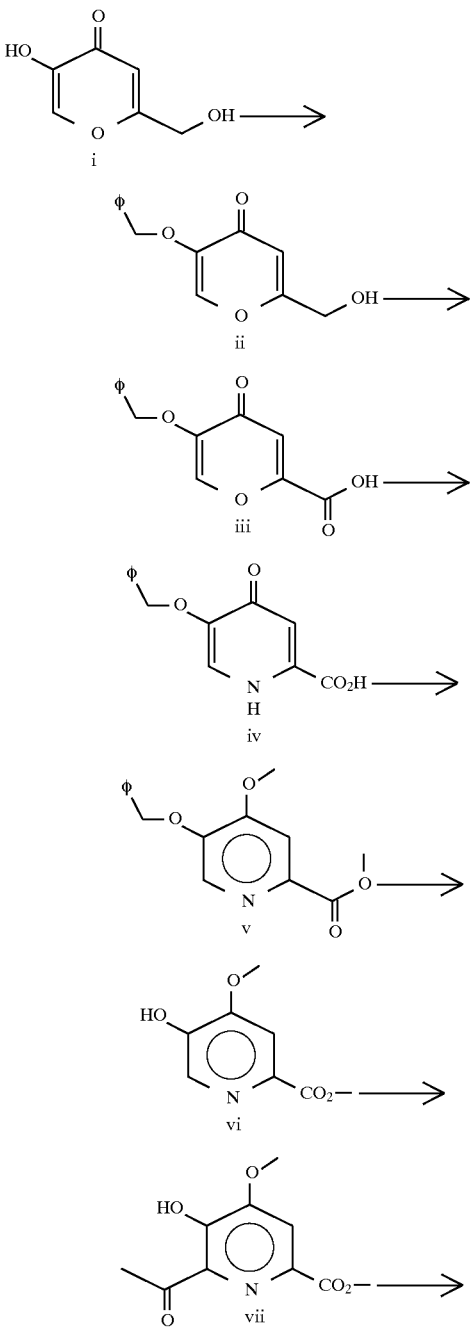

-continued
SCHEME I

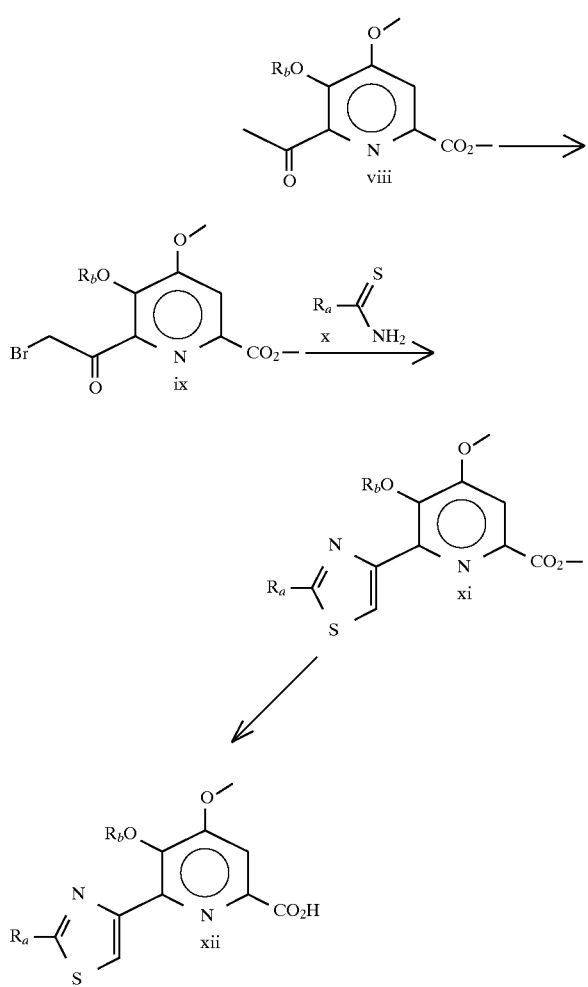

SCHEME II

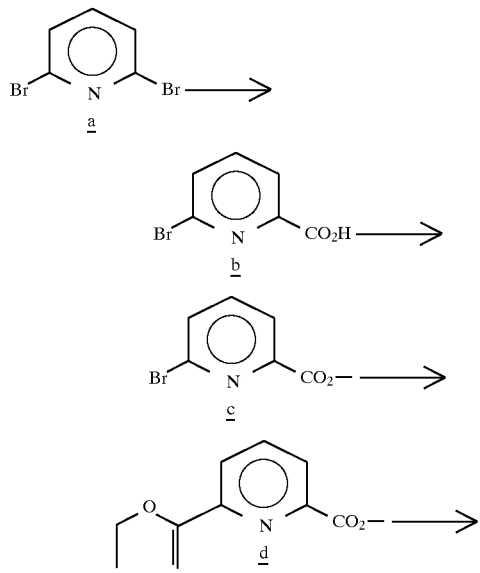

-continued
SCHEME II

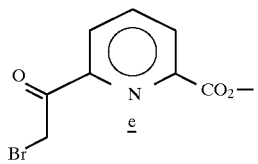

SCHEME III

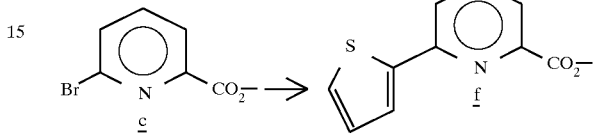

The compounds of the present invention can be prepared and administered in a wide variety of oral and parenteral dosage forms. Thus, the compounds of the present invention can be administered by injection, that is, intravenously, intramuscularly, intra-cutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of the present invention, such as a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use as inhibitors of endothelin converting enzyme the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting example illustrates the inventors' preferred methods for preparing the compounds of the invention.

INTERMEDIATE 1
2-Hydroxymethyl-5-benzyloxy-γ-pyrone

Solid sodium (5.05 g, 0.22 mol) was dissolved in methanol (400 mL) to which solid Kojic acid (28.4 g, 0.2 mol) was added. To the resulting solution was added benzyl chloride (25.4 mL, 0.22 mol), and the reaction mixture was refluxed 18 hours. The mixture was cooled and poured into stirred water (400 mL). The white precipitate formed was isolated by filtration, washed with water (400 mL), and dried in vacuo to give Intermediate 1 as a white solid (31.8 g, 69%). CIMS, m/e (relative intensity) 233 (MH$^+$, 45), 91 (100); $^1$H nmR (CDCl$_3$): δ 7.52 (s, 1H), 7.38 (m, 5H), 6.52 (s, 1H), 5.06 (s, 2H), 4.45 (s, 2H). Analysis calculated for ($C_{13}H_{12}O_4$): Found: C, 66.94; H, 5.11; N, 0.02.

INTERMEDIATE 2
5-Benzyloxy-4-oxo-4H-pyran-2-carboxylic acid

To an acetone (1.6 L) solution of Intermediate 1 (32.8 g, 0.14 mol) at 0° was added Jones Reagent (100 mL, 8.7N). The dark mixture was stirred for 3 hours at 0°. Isopropanol (30 mL) was added to the mixture which was then stirred at room temperature for 1 hour. The chromium salts were removed by filtration through celite, and the filtrate concentrated to approximately 250 mL. The slurry was allowed to stand 18 hours at room temperature and filtered. The solid was air-dried 2 hours to give Intermediate 2 as a pale green solid (21.7 g, 63%). CIMS, m/e (relative intensity) 247 (MH$^+$, 10), 246 (4), 91(100).

$^1$H nmR (d$_6$-DMSO): δ 8.38 (s, 1H), 7.43(m, 5H), 6.94 (s, 1H), 4.98 (s, 2H). Analysis calculated for ($C_{13}H_{10}O_5$·0.25 H$_2$O): Found: C, 62.28; H, 4.05; N, 0.02.

INTERMEDIATE 3
5-Benzyloxy-4-oxo-1,4-dihydro-pyridine-2-carboxylic acid

A solution of Intermediate 2 (21.64 g, 87.9 mol) in NH$_4$OH (600 mL) was sealed in a 2-L stainless steel reactor and heated to 90° for 5.5 hours. The resulting orange solution was evaporated to a pink solid and dissolved in H$_2$O (250 mL). The pH was adjusted to 2.0 (6N HCl). The precipitate was isolated by filtration and dried in vacuo at 60° for 18 hours to give Intermediate 3 as a pink solid (17.11 g, 79%). CIMS, m/e (relative intensity) 246 (MH$^+$, 22), 245 (3), 91 (100).

$^1$H nmR (d$_6$-DMSO): δ 7.91 (br s, 1H), 7.4–7.0 (m, 7H), 5.19 (s, 2H).

INTERMEDIATE 4
5-Benzyloxy-4-methoxy-1,4-dihydro-pyridine-2-carboxylic acid methyl ester To a 20% methanol/toluene slurry (100 mL) of Intermediate 3 (5.80 g, 23.7 mmol) was added TMSCHN$_2$ in hexanes (2.0M, 35 mL, 70 mmol) dropwise. The slurry was stirred 2 hours, and the resulting solution was evaporated to an oil. Flash chromatography of the crude product on silica gel using 25% EtOAc/CH$_2$Cl$_2$ gave Intermediate 4 as a off-white solid (3.13 g, 48%). CIMS, m/e (relative intensity) 274 (MH$^+$, 100), 273 (17), 91 (90).

$^1$H nmR (CDCl$_3$): δ 8.24 (s, 1H), 7.71 (s, 1H), 7.4 (m, 5H), 5.27 (s, 2H), 3.99 (s, 3H), 3.98 (s, 3H).

INTERMEDIATE 5
5-Hydroxy-4-methoxy-pyridine-2-carboxylic acid methyl ester

A methanol (100 mL) solution of Intermediate 4 (2.07 g, 7.57 mmol) was stirred in an hydrogen atmosphere in the presence of 10% Pd/C (500 mg) for 1.5 hours. The catalyst was removed by filtration through celite. The celite was washed with methanol (200 mL) and ethyl acetate (50 mL). The filtrate was evaporated to give Intermediate 5 as an off-white solid (1.31 g, 94%). CIMS, m/e (relative intensity) 184 (MH$^+$, 45), 152 (46), 125 (42).

$^1$H nmR (d$_6$-DMSO): δ 10.4 (br s, 1H), 8.09 (s, 1H), 7.62 (s, 1H), 3.91 (s, 3H), 3.83 (s, 3H). Analysis calculated for ($C_8H_9NO_4$): Found: C, 52.26; H, 4.86; N, 7.48.

INTERMEDIATE 6
6-Acetyl-5-hydroxy-4-methoxy-pyridine-2-carboxylic acid methyl ester To an ice-cooled solution of Intermediate 5 (2.10 g, 11.4 mmol) and acetaldehyde (3.8 mL, 68 mmol) in 3N H$_2$SO$_4$ (10 mL) was added concurrently 70% t-butyl hydroperoxide (6.6 mL, 48 mmol) and an aqueous solution (50 mL) of FeSO$_4$.7H$_2$O (19.1 g, 69 mmol) over 15 minutes. The resulting red solution was stirred 2 hours while allowing to warm to approximately 20°. Solid $Na_2SO_3$ was added until starch-iodide paper was negative. The reaction mixture was extracted with $CH_2Cl_2$ (3×100 mL), and the combined washings were dried ($MgSO_4$) and evaporated to give the crude product. Flash chromatography of the crude product on silica gel using 2% methanol/$CHCl_3$ gave Intermediate 6 as a white solid (0.78 g, 30%). CIMS, m/e (relative intensity) 226 ($MH^+$, 100), 225 (19), 194 (20).

$^1H$ nmR ($CDCl_3$): δ 12.43 (s, 1H), 7.73(s, 1H), 7.22 (s, 1H), 3.98 (s, 3H), 3.95 (s, 3H), 2.80 (s, 3H).

INTERMEDIATE 7
6-Acetyl-4,5-dimethoxy-pyridine-2-carboxylic acid methyl ester To a solution of Intermediate 6 (0.70 g, 3.11 mmol) in 20% methanol/toluene (30 mL) was added $TMSCHN_2$ in hexanes (2.0M, 5.0 mL, 10.0 mmol) dropwise over 2 hours. The solvent was evaporated, and the residue dissolved in chloroform. The chloroform solution was washed with 1N NaOH and brine, dried ($MgSO_4$), and evaporated to a yellow oil. Flash chromatography of the crude product on silica gel using 5% EtOAc/$CH_2Cl_2$ gave Intermediate 7 as a white solid (0.36 g, 49%). CIMS, m/e (relative intensity) 240 ($MH^+$, 100), 208 (7), 179 (6).

$^1H$ nmR ($CDCl_3$): δ 7.80 (s, 1H), 4.01 (s, 3H), 4.00 (s, 3H), 3.96 (s, 3H), 2.68 (s, 3H). Analysis calculated for: ($C_{11}H_{13}NO_5$): Found: C, 55.36; H, 5.39; N, 5.75.

INTERMEDIATE 8
6-Bromoacetyl-4,5-dimethoxy-pyridine-2-carboxylic acid methyl ester To an acetic acid (20 mL) solution of Intermediate 7 (748 mg, 3.13 mmol) was added 31% HBr in acetic acid (1.25 mL, 6.49 mmol) and pyridinium bromide perbromide (1.05 g, 3.29 mmol). The slurry was stirred at room temperature 4.5 hours. The acetic acid was evaporated, and the solid was partitioned between water (30 mL) and ethyl acetate (100 mL). The organic layer was separated, washed aqueous with additional ethyl acetate (50 mL), dried ($MgSO_4$) combined organic layers, and evaporated to give Intermediate 8 as a tan solid (940 mg, 94%). The product was using without additional purification, but can be further purified by flash chromatography on silica gel using 10% EtOAc/$CH_2Cl_2$. CIMS, m/e (relative intensity) 320 ($MH^+$, 46), 318 (48), 240 (100).

$^1H$ nmR ($CDCl_3$): δ 7.82 (s, 1H), 4.72 (s, 2H), 4.00 (m, 9H). Analysis calculated for: ($C_{11}H_{12}BrNO_5 \cdot 0.05HBr$): Found: C, 41.01; H, 3.48; N, 4.42; Br, 25.70.

INTERMEDIATE 9
7-Oxo-octanoic acid amide

To a benzene (15 mL) solution of 7-oxo-octanoic acid (1.58 g, 10 mmol) was added oxalyl chloride (1.30 mL, 15 mmol). The solution was stirred for 2 hours at room temperature and evaporated to an oil which was dissolved in diethyl ether (35 mL). Ammonia was bubbled through the solution giving a white precipitate. The slurry was filtered, and the solid extracted with ethyl acetate (30 mL) and chloroform (50 mL). The extracts were evaporated to give Intermediate 9 as an off-white solid (1.38 g, 88%). CIMS, m/e (relative intensity) 158 ($MH^+$, 20), 95 (100).

$^1H$ nmR ($CDCl_3$): δ 5.5 (br s, 2H), 2.44 (t, 2H), 2.22 (t, 2H), 2.12 (s, 3H), 1.3–1.6 (m, 6H).

INTERMEDIATE 10
7-Hydroxy-octanoic acid amide

Solid $NaBH_4$ (5.65 g, 149 mmol) was added in portions to a methanol (100 mL) solution of Intermediate 9 (4.69 g, 29.8 mmol) at 0°. After 30 minutes additional $NaBH_4$ (2.00 g, 52.8 mmol) was added. The slurry was stirred 2 hours while allowing bath temperature to rise to approximately 15°. The solvent was evaporated, and the residue dissolved in 1N HCl (10 mL) and saturated $NH_4Cl$ (30 mL). The solution was extracted with ethyl acetate (3×150 mL). The organic washings were combined, dried ($MgSO_4$) and evaporated to give Intermediate 10 as a white solid (3.09 g, 65%). CIMS, m/e (relative intensity) 160 ($MH^+$, 30), 142 (100).

$^1H$ nmR ($CD_3$): δ 3.7 (m, 1H), 2.20 (t, 2H), 1.62 (m, 2H), 1.4 (m, 6H), 1.14 (d, 3H). Analysis calculated for ($C_8H_{17}NO_2$): Found: C, 60.36; H, 10.85; N, 8.78.

INTERMEDIATE 11
7-Acetoxy-octanoic acid amide

To a pyridine (10 mL) solution of Intermediate 10 (0.65 g, 4.1 mmol) was added acetic anhydride (0.62 mL, 6.5 rmnol). The solution was stirred 18 hours at room temperature. The solvent was evaporated to give an oil which was dissolved in water. The pH of the aqueous solution was adjusted to 2 (1N HCl) and extracted with ethyl acetate (2×50 mL). The combined extracts were washed with saturated $NaHCO_3$, dried ($MgSO_4$) and evaporated to give Intermediate 11 as a pale yellow oil (0.73 g, 89%). CIMS, m/e (relative intensity) 202 ($MH^+$, 29), 142 (100).

$^1H$ nmR ($CDCl_3$): δ 5.4 (br s, 2H), 4.88 (m, 1H), 2.22 (t, 2H), 2.02 (s, 3H), 1.3–1.7 (m,8H), 1.19 (d, 3H).

INTERMEDIATE 12
7-Acetoxy-octathioic acid amide

Solid Lawesson's reagent (1.06 g, 2.62 mmol) was added to a slurry of Intermediate 11 (0.87 g, 4.32 mmol) and THF (20 mL). The slurry was stirred for 2 hours, and the THF was evaporated. The residue was dissolved in chloroform (50 mL) and washed with 30 mL each 1N HCl, water, and saturated $NaHCO_3$. The organic layer was dried ($MgSO_4$) to give the crude product as an oil. Flash chromatography of the crude product on silica gel using 20% EtOAc/$CH_2Cl_2$ gave Intermediate 12 as a colorless oil (0.58 g, 62%). CIMS, m/e (relative intensity) 218 ($MH^+$, 74), 158 (100).

$^1H$ nmR ($CDCl_3$): δ 7.5 (br s, 1H), 6.9 (br s, 1H). 4.88 (m, 1H), 2.65 (t, 2H), 2.03 (s, 3H), 1.3–1.8 (m, 8H), 1.20 (d, 3H).

INTERMEDIATE 13
6-[2-(6-Acetoxy-heptyl)-thiazol-4-yl]-4,5-dimethoxy-pyridine-2-carboxylic acid methyl ester To an acetone (10 mL) solution of Intermediate 8 (0.76 g, 2.4 mmol) was added Intermediate 12 (0.52 g, 2.4 mmol), and the solution was stirred 18 hours in the dark at room temperature. The solvent was evaporated and the oil dissolved in methanol (20 mL). To the a solution was added activated (1N NaOH) Dowex 1-X2 anion exchange resin (approximately 5 g), and the slurry was allowed to stand 15 minutes. The slurry was filtered, and the resin washed with methanol (100 mL). The washings were concentrated to approximately 30 mL. The solution was made acidic (few drops 1N HCl) and refluxed 30 minutes. The solution was evaporated to give the crude product as an oil. Flash chromatography of the crude product on silica gel using first 10% EtOAc/$CH_2Cl_2$ then 4% MeOH/$CHCl_3$ gave Intermediate 13 as an oil (344 mg, 33%). CIMS, m/e (relative intensity) 437 ($MH^+$, 100), 377 (34).

$^1H$ nmR ($CDCl_3$): δ 7.91 (s, 1H), 7.73 (s, 1H), 4.88 (m, 1H), 4.02 (s, 3H), 3.97 (s, 3H), 3.89 (s, 3H),3.10 (t, 2H), 2.02 (s, 3H), 1.3–1.8 (m, 8H), 1.20 (d, 3H).

EXAMPLE 1
6-[2-(6-Hydroxy-heptyl)-thiazol-4-yl]-4,5-dimethoxy-pyridine-2-carboxylic acid (WS75624B)

A cloudy solution of Intermediate 13 (0.32 g, 0.74 mmol) in 0.5N NaOH (15 mL) and THF (10 mL) was heated to 60° for 2 hours. The THF was evaporated from the cooled solution and saturated NH$_4$Cl (20 mL) was added. The aqueous layer was extracted with chloroform (50 mL) and methylene chloride (50 mL). The organic layer was washed with saturated NH$_4$Cl and 1N HCl. After drying (MgSO$_4$) the organic layer was evaporated to give Example 1 as a off-white solid (0.20 g, 71%). APCIMS, m/e (relative intensity) 381.5 (MH$^+$, 100), 337.6 (36).

$^1$H nmR (CD$_3$OD): δ 8.35 (s, 1H), 7.83 (s, 1H), 4.08 (s, 3H), 3.99 (s, 3H), 3.67 (m, 1H) 3.11 (t, 2H), 1.84 (m, 2H), 1.4 (br m, 6H), 1.10 (d, 3H). HPLC (1:1 CH$_3$CN:H$_2$O, C$_{18}$) room temperature 2.38 minutes, (98.7%), at 254 nm, mp 153°. Analysis calculated for (C$_{18}$H$_{24}$N$_2$O$_5$S·0.2HCl) Found: C, 55.68; H, 6.33; N, 6.84.

INTERMEDIATE 14
6-(2-Methyl-thiazol-4-yl)-4,5-dimethoxy-pyridine-2-carboxylic acid methyl ester To an acetone (3 mL) solution of Intermediate 8 (184 mg, 0.579 mmol) was added thioacetamide (48 mg, 0.64 mmol), and the solution stirred in the dark 18 hours. The resulting slurry was filtered, and the solid washed with acetone (2 mL). The solid was dissolved in methanol (15 mL), and the solution was refluxed 30 minutes. To the cooled solution was added activated (1N NaOH) Dowex 1-X2 (approximately 0.5 g), and the slurry allowed to stand 15 minutes. The slurry was filtered and washed with methanol (30 mL). The filtrate was evaporated to give Intermediate 14 as an oil which solidified upon standing (136 mg, 80%). CIMS, m/e (relative intensity) 295 (MH$^+$, 100), 234 (13).

$^1$H nmR (CDCl$_3$): δ 7.87 (s, 1H), 7.68 (s, 1H), 3.97 (s, 3H), 3.93 (s, 3H), 3.84 (s, 3H ), 2.75 (s, 3H).

EXAMPLE 2
6-(2-Methyl-thiazol-4-yl)-4,5-dimethoxy-pyridine-2-carboxylic acid A solution of Intermediate 14 (132 mg, 0.449 mmol) in THF (2 mL) and 0.5N NaOH (5 mL) was heated to 50° for 2 hours. The THF was removed from the cooled solution by evaporation. Additional water (15 mL) was added to the reaction mixture, and the pH adjusted to 4.5 (1N HCl). The aqueous layer was extracted with chloroform (3×25 mL). The extracts were combined, dried (MgSO$_4$), and evaporated to give Example 2 as a white foam which was dried in vacuo for 5 hours at 60° (96 mg, 77%). CIMS, m/e (relative intensity) 281 (MH$^+$, 100), 237 (49).

$^1$H nmR (CDCl$_3$): δ 7.99 (s, 1H), 7.76 (s, 1H), 4.00 (s, 3H), 3.89 (s, 3H), 2.74 (s, 3H). HPLC (1:1 CH$_3$CN:H$_2$O, C$_{18}$) room temperature 3.17 minutes, (99.3%), at 254 nm, mp 126°–127°. Analysis calculated for (C$_{12}$H$_{12}$N$_2$O$_4$S·0.55 HCl): Found: C, 48.32; H, 4.81; N, 9.00.

INTERMEDIATE 15
Octanthioic acid amide

A slurry of octanoic acid amide (605 mg, 4.22 mmol) and Lawesson's reagent (854 mg, 2.11 mmol) in THF (15 mL) was stirred 2 hours at room temperature. The solvent was evaporated and the residue dissolved in chloroform (50 mL). This solution was washed with 30 mL each 1N HCl, water, and saturated NaHCO$_3$. The solution was then dried (MgSO$_4$) and evaporated to give the crude product. Flash chromatography of the crude product on silica gel using 5% EtOAc/CH$_2$Cl$_2$ gave Intermediate 15 as a white solid (472 mg, 70%). CIMS, m/e (relative intensity) 160 (MH$^+$, 100), 126 (43).

$^1$H nmR (CDCl$_3$): δ 7.6 (br s, 1H), 6.9 (br s, 1H), 2.65 (t, 2H), 1.79 (t, 2H), 1.3 (m, 8H), 0.87 (m, 3H). Analysis calculated for (C$_8$H$_{17}$NS): Found: C, 60.47; H, 10.79; N, 8.58; S, 19.89.

INTERMEDIATE 16
6-(2-Heptyl-thiazol-4-yl)-4,5-dimethoxy-pyridine-2-carboxylic acid methyl ester To an acetone (2 mL) solution of Intermediate 8 (101 mg, 0.317 mmol) was added Intermediate 15 (57 mg, 0.36 mmol), and the solution stirred 18 hours at room Etemperature. Ethyl acetate (10 mL) was added to the cloudy mixture giving a precipitate which was collected by filtration, and the solid was washed with ethyl acetate. The crude product was dissolved in methanol, and this solution was added to a methanol slurry of activated (1N NaOH) Dowex 1-X2 (approximately 0.5 g). The slurry allowed to stand 15 minutes and filtered. The resin was washed with methanol (30 mL). The filtrate was evaporated to give Intermediate 16 as an oil (77 mg, 66%). CIMS, m/e (relative intensity) 379 (MH$^+$, 100), 294 (27).

$^1$H nmR (CDCl$_3$): δ 7.92 (s, 1H), 7.73 (s, 1H), 4.02 (s, 3H), 3.98 (s, 3H), 3.80 (s, 3H), 3.10 (t, 2H), 1.8 (m, 2H), 1.4–1.2 (m, 8H), 0.88 (m, 3H).

EXAMPLE 3
6-(2-Heptyl-thiazol-4-yl)-4,5-dimethoxy-pyridine-2-carboxylic acid A solution of Intermediate 16 (91 mg, 0.24 mmol) in THF (2 mL) and 0.5N NaOH (5 mL) was heated to 50° for 2 hours. The THF was removed from the cooled solution by evaporation. Additional water (15 mL) was added to the reaction mixture, and the pH adjusted to 5 (1N HCl). The aqueous layer was extracted with chloroform (2×15 mL). The extracts were combined, dried (MgSO$_4$), and evaporated to give Example 3 as an off-white solid which was dried in vacuo for 4 hours at 60° (85 mg, 98%). CIMS, m/e (relative intensity) 365 (MH$^+$, 88), 379 (100).

$^1$H nmR (CDCl$_3$): δ 8.10 (s, 1H), 7.80 (s, 1H), 4.03 (s, 3H), 4.00 (s, 3H), 2.3 (m, 2H), 1.2–0.7 (m, 13H). HPLC (1:1 CH$_3$CN:H$_2$O, C$_{18}$) room temperature 3.48 minutes, (95.06%), at 254 nm, mp 257° (dec). Analysis calculated for (C$_{18}$H$_{24}$N$_2$O$_4$S·0.6 HCl): Found: C, 56.11; H, 6.05; N, 6.98; S, 8.47.

INTERMEDIATE 17
6-(2-Amino-thiazol-4-yl)-4,5-dimethoxy-pyridine-2-carboxylic acid methyl ester To an acetone (5 mL) solution of Intermediate 8 (0.25 g, 0.786 mmol) was added thiourea (65 mg, 0.85 mmol), and the solution stirred 18 hours at room temperature. The resulting precipitate was collected by filtration, and the solid was washed with ethyl acetate. The crude product was dissolved in methanol (20 mL), and this solution was added to a methanol slurry of activated (iN NaOH) Dowex 1-X2 (approximately 1 g). The slurry was allowed to stand 15 minutes and filtered. The resin was washed with methanol (30 mL). The methanol solution was made acidic (few drops 1N HCl) and refluxed 30 minutes. The solution was evaporated to give Intermediate 17 as an oil (0.11 g, 48%). CIMS, m/e (relative intensity) 296 (MH$^+$, 100), 280 (6).

$^1$H nmR (CD$_3$OD): δ 7.85 (s, 1H), 7.72 (s, 1H), 4.09 (s, 3H), 4.07 (s, 3H), 4.06 (s, 3H).

EXAMPLE 4
6-(2-Amino-thiazol-4-yl)-4,5-dimethoxy-pyridine-2-carboxylic acid

A solution of Intermediate 17 (0.15 g, 0.51 mmol) in THF (4 mL), methanol (2 mL) and 1N NaOH (4 mL) was stirred at room temperature for 1 hour. The pH of the reaction mixture was adjusted to 3 (1N HCl), and the slurry concentrated to approximately 5 mL. Water (5 mL) was added to the slurry, and the precipitate collected by filtration. The solid was washed with water (2 mL), acetone (2 mL), ethyl acetate (2 mL), and diethyl ether (5 mL). The solid was dried in vacuo to give Example 4 as a tan solid (81 mg, 57%). CIMS, m/e (relative intensity) 282 (MH$^+$, 100), 262 (46).

$^1$H nmR (d$_6$-DMSO): δ 7.73 (s, 1H), 7.48 (s, 1H), 4.02 (s, 3H), 3.90 (s, 3H), mp 193° (dec). Analysis calculated for (C$_{11}$H$_{11}$N$_3$O$_4$S·2.1 HCl): Found: C, 36.75; H,4.07; N, 11.61.

INTERMEDIATE 18
6-(2-N-Methylamino-thiazol-4-yl)-4,5-dimethoxy-pyridine-2-carboxylic acid methyl ester To an acetone (5 mL) solution of Intermediate 8 (0.24 g, 0.75 mmol) was added N-methylthiourea (75 mg, 0.83 mmol), and the solution was stirred 4 hours in the dark at room temperature. The resulting precipitate was collected by filtration, and the solid was washed with acetone (5 mL) and diethyl ether (5 mL). The crude product was dissolved in methanol (20 mL), and this solution was added to a methanol slurry of activated (1N NaOH) Dowex 1-X2 (approximately 1 g). The slurry was allowed to stand 15 minutes and filtered. The resin was washed with methanol (30 mL). The methanol solution was made acidic (few drops 1N HCl) and refluxed 30 minutes. The solution was evaporated to give the crude product. Flash chromatography of the crude product on silica gel using 89:10:1 CHCl$_3$:MeOH:NH$_4$OH gave Intermediate 18 as a white solid (110 mg, 48%). CIMS, m/e (relative intensity) 310 (MH$^+$, 100).

$^1$H nmR (CD$_3$OD): δ 7.76 (s, 1H), 7.17 (s, 1H), 4.03 (s, 3H), 3.92 (s, 3H), 3.85 (s, 3H), 2.98 (s, 3H).

EXAMPLE 5
6-(2-N-Methylamino-thiazol-4-yl)-4,5-dimethoxy-pyridine-2-carboxylic acid A solution of Intermediate 18 (109 mg, 0.35 mmol) in THF (2 mL), methanol (2 mL) and 1N NaOH (2 mL) was stirred at room temperature for 1 hour. The pH of the reaction mixture was adjusted to 4 (1N HCl), and the slurry concentrated to approximately 5 mL. Water (5 mL) was added to the slurry, and the precipitate collected by filtration. The solid was washed with water (2 mL) and dried in vacuo to give Example 5 as a pale yellow solid (86 mg, 83%). CIMS, m/e (relative intensity) 296 (MH$^+$, 23), 223 (100).

$^1$H nmR (CD$_3$OD): δ 7.77 (s, 1H), 7.65 (s, 1H), 4.10 (s, 3H), 4.06 (s, 3H), 3.09 (s, 3H), mp 172° (dec). Analysis calculated for (C$_{12}$H$_{13}$N$_3$O$_4$S·1.6HCl): Found: C, 40.57; H,4.42; N, 11.69.

INTERMEDIATE 19
6-(Thiazol-4-yl)-4,5-dimethoxy-pyridine-2-carboxylic acid methyl ester To an acetone (3 mL) solution of Intermediate 8 (246 mg, 0.77 mmol) was added thioformamide (100 mg, 1.6 mmol), and the solution was stirred 18 hours in the dark at room temperature. The resulting precipitate was collected by filtration, and the solid was washed with acetone (2 mL) and diethyl ether (10 mL). The crude product was dissolved in methanol (20 mL), and this solution was added to a methanol slurry of activated (1N NaOH) Dowex 1-X2 (approximately 1 g). The slurry was allowed to stand 15 minutes and filtered. The resin was washed with methanol (50 mL). The filtrate was evaporated to give Intermediate 19 as an off-white solid (109 mg, 50%). CIMS, m/e (relative intensity) 281 (MH$^+$, 100).

$^1$H nmR (CD$_3$OD): δ 9.09 (m, 1H), 8.20 (m, 1H), 7.82 (s, 1H) 4.09 (s, 3H), 4.05 (s, 3H), 3.96(s, 3H).

EXAMPLE 6
6-(Thiazol-4-yl)-4,5-dimethoxy-pyridine-2-carboxylic acid

A solution of Intermediate 19 (100 mg, 0.357 mmol) in THF (4 mL), methanol (1 mL) and 1N NaOH (4 mL) was stirred at room temperature for 1 hour. The solvent was evaporated, and the residue was dissolved in water (15 mL). The aqueous layer was washed with ethyl acetate (10 mL) and the pH adjusted to 5 (2N HCl). The aqueous layer was extracted with chloroform (2×30 mL). The extracts were combined, dried (MgSO$_4$), and evaporated to give Example 6 as an off-white solid which was dried in vacuo for 3 hours at 60° (66 mg, 69%). APCIMS, m/e (relative intensity) 267.4 (MH$^+$, 100), 223.3 (19).

$^1$H nmR (CD$_3$OD): δ 9.22 (br s, 1H), 8.56 (m, 1H), 7.88 (s, 1H) 4.11 (s, 3H), 4.03 (s, 3H). HPLC (1:1 CH$_3$CN:H$_2$O, C$_{18}$) room temperature 3.08 minutes, (99.75%), at 254 nm, mp 185° (dec). Analysis calculate for (C$_{11}$H$_{10}$N$_2$O$_4$S·0.4 HCl): Found: C, 46.82; H,4.11; N, 9.78.

We claim:

1. A compound of formula

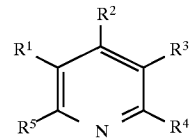

or a pharmaceutically acceptable salt thereof, wherein R$^1$, R$^2$, and R$^3$ are each independently selected from hydrogen;

halogen;

alkyl which is straight, or cyclic unsubstituted or substituted by from 1 to 4 substituents each independently selected from halogen, amino, monoalkylamino, dialkylamino, hydroxy, alkoxy, nitro, aryl, cyano, or carboxyl;

alkoxy;

monoalkylamino;

dialkylamino;

nitro;

cyano;

hydroxy;

carboxyl;

carboxamide;

monoalkylcarboxamide;

dialkylcarboxamide;

thioalkyl;

thiol; and

SO$_3$H;

provided that R1, R2, R3 are not simultaneously hydrogen R$^4$ is R$^6$

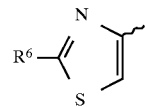

wherein R$^6$ is hydrogen, straight or branched alkyl which is unsubstituted; and wherein R$^6$ is amino, monoalkylamino, dialkylamino, or halogen;

$R^4$ is also

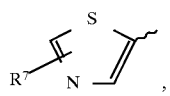, wherein $R^7$ is hydrogen or alkyl of from 1 to 4 carbon atoms which alkyl is unsubstituted or substituted by from 1 to 4 substituents each independently selected from halogen, amino, thiol, monoalkylamino, dialkylamino, nitro, cyano, hydroxy, alkoxy, carboxyl, aryl or $SO_3H$;

$R^8$ is alkyl straight or branched; and $R^5$ is $CO_2H$; $CH_2OH$;

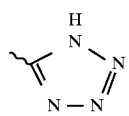

2. A compound selected from 6-(2-Methyl-thiazol-4-yl)-4,5-dimethoxy-pyridine-2-carboxylic acid, 6-(2-Heptyl-thiazol-4-yl)-4,5-dimethoxy-pyridine-2-carboxylic acid, 6-(2-Amino-thiazol-4-yl)-4,5-dimethoxy-pyridine-2-carboxylic acid, 6-(2-N-Methylamino-thiazol-4-yl)-4,5-dime-thoxy-pyridine-2-carboxylic acid, and 6-(Thiazol-4-yl)-4,5-dimethoxy-pyridine-2-carboxylic acid.

3. A pharmaceutical composition comprising a therapeutically effective amount of a compound according to claim 1.

4. A method of treating pulmonary hypertension comprising administering to a host suffering therefrom a therapeutically effective amount of a compound according to claim 1 in unit dosage form.

* * * * *